United States Patent [19]

de Andrade Brüning

[11] Patent Number: 5,163,982
[45] Date of Patent: Nov. 17, 1992

[54] PROCESS TO FIND STABILITY OF OIL MIXTURES, INCLUDING SHALE OIL AND FRACTIONS THEREOF

[75] Inventor: Inái M. R. de Andrade Brüning, Rio de Janeiro, Brazil

[73] Assignee: Petroleo Brasileiro S.A. - Petrobras, Rio De Janeiro, Brazil

[21] Appl. No.: 774,947

[22] Filed: Oct. 11, 1991

[30] Foreign Application Priority Data

Oct. 12, 1990 [BR] Brazil ................................. 9005133

[51] Int. Cl.⁵ ........................................... G01N 30/02
[52] U.S. Cl. ....................................... 55/67; 210/635; 210/656; 422/89; 436/60; 436/140; 436/161
[58] Field of Search .................... 210/656, 635, 198.2; 55/67, 197, 386; 436/60, 140, 161; 422/89, 104

[56] References Cited

U.S. PATENT DOCUMENTS 4,889,813 12/1989 de Andrade Bruning ........... 436/60

FOREIGN PATENT DOCUMENTS 2207246 1/1989 United Kingdom ............. 210/198.2

Primary Examiner—Ernst G. Therkorn
Attorney, Agent, or Firm—Sughrue, Mion, Zinn, Macpeak & Seas

[57] ABSTRACT

A process to find the stability of mixtures of oils, including that of shale oils, and of distilled fractions of petroleum oils is described, which process may be extended to any mixtures of non-ionic compounds containing a non-polar hydrocarbon moiety and a heteroatomic polar moiety, and such polar and non-polar moieties may lie in the same or different molecules.

12 Claims, 3 Drawing Sheets

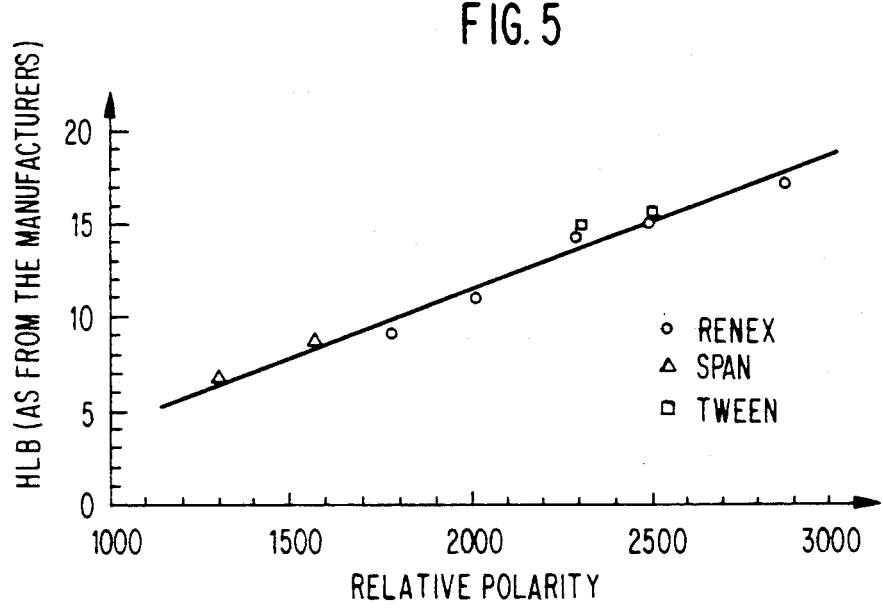

PROCESS TO FIND STABILITY OF OIL MIXTURES, INCLUDING SHALE OIL AND FRACTIONS THEREOF

BACKGROUND OF THE INVENTION

This invention deals with a process to find the stability of oil mixtures, including shale oils and distilled fractions thereof. More precisely, the invention concerns a process to determine the stability of oil mixtures, including shale oils, as well as the distilled fractions thereof, by measuring the chemical polarity of such mixtures.

This invention is also intended to determine the chemical stability of any carbohydrate mixtures usually met with in oils from several sources, and contaminated by nitrogen, sulphur and exygen compounds.

The stability of an oil mixture is the direct outcome of its chemical polarity, since polar substances are the chemically reactive ones and consequently the more unstable ones. Hence by finding the chemical polarity of a mixture its stability can be gauged, that is, the lower its chemical polarity, numerically, the more stable and of better quality will the mixture be.

Measurement of the chemical stability of oil mixtures is likewise useful in the case of emulsions of oil mixtures in water. Whenever such emulsions have to be broken by means of a non-ionic surfactant the chemical polarity of the surfactant must be greater than that of the emulsion of the oil mixture in water, in order to displace the natural oil surfactants at the water-oil interface. The higher the polarity of an oil or oil mixture the better it will emulsify water and the polarity of a de-emulsifier to break such emulsion must be still higher. The process used in this invention as shown herein provides an answer to this question, since by measuring just one number—that of chemical polarity—non-ionic surfactant most suitable to separate a given emulsion of oils or of oil mixtures can be found. Hence the inventive process is aimed at finding what proportion of each oil there has to be in a given mixture in order to arrive at a given chemical polarity. An emulsion of oils in water may be destabilized with the aid of any non-ionic surfactant that has a chemical polarity higher than that of the oil mixture. It should be noted that a non-ionic surfactant molecule, since it is an amphyphilic kind of substance, contains both non-polar and polar groups in the same molecule, the non-polar moiety being a chain of hydrocarbons and the polar one being brought about by functional organic groups. Hence the polar and non-polar moieties in oils are made up of different molecules: hydrocarbons, thiophenes, etc. In the amphyphilic compounds, however, polar and non-polar moieties are both in the same molecule. The inventive process, namely, to measure the chemical stability of oil mixtures by measuring the chemical polarity of such mixtures, also applies to non-ionic surfactant mixtures, to finding the lowest chemical polarity needed for a surfactant to break an oil/water emulsion of known chemical polarity, etc.

Therefore the chemical polarity of any mixtures of non-ionic compounds containing both non-polar and polar moieties, whether or not such polar and non-polar moities make up separate molecules or one same molecule (as occurs with a great many organic, pharmaceutical and biologically active compounds), may be found, thus enabling the best proportion of each component of the mixture for a given application to be arrived at.

PRIOR ART

Under Brazilian patent application no. PI 8703790, lodged by the present applicant as well, and here fully incorporated as reference, a process to find the chemical polarity of oil and of the heavy fractions thereof is provided, which serves to show that the relative polarity of oils may be quantified with the aid of a single number, that classifies several oils in terms of their quality and therefore stability. The quantification of the relative polarity of oils has several applications. For instance, where oil has been discovered but is not yet being produced, any problems in connection with the exploring of reservoirs, designing of production, treatment and transportation systems, planning of production operations and of refining procedures can be dealt with beforehand, thus enabling a great saving in costs to take place.

SUMMARY OF THE INVENTION

The present invention herewith discloses a further development in the field of research into the chemical polarity of oils, this time concerning oil mixtures, including shale oils and mixtures of oil fractions, as well as mixtures of oil emulsions in water and mixtures of any compounds therein, whether within the same or different molecules, non-polar, hydrocarbon moieties, and polar moieties, containing hereoatoms, results arrived at having not yet been announced nor hinted at within literature on the subject.

Therefore, one objective of this invention is to provide a process to determine the stability of oil mixtures, including mixtures of oils from different sources and of different quality, of ordinary oils mixed with shale oils, as well as mixtures of different shale oils or mixtures of fractions thereof, and also mixtures of any different hydrocarbon cuts contaminated by nitrogen, sulphur and oxygen compounds.

Another objective is to determine, again by means of their chemical polarity, the stability of mixtures of different oils, so as to enable the best quantity of each constituent of the mixture to be picked out, thereby meeting most suitable quality requirements for intended use.

Still another objective of this invention is to find the chemical polarity of oil mixtures or of fractions thereof, emulsified in water, in order to pick the best non-ionic surfactant or mixtures thereof able to break emulsions of oil mixtures in water, for which the non-ionic surfactant or mixtures thereof must have a chemical polarity higher than that of the emulsion of oil mixtures in water.

One more objective is to find chemical stability for any end use, by measurement of the chemical polarity of mixtures of non-polar compounds, such as hydrocarbons, and of nitrogen, sulphur and oxygen polar compounds, both polar and non-polar moieties belonging to the same molecule or comprising separate molecules.

The process developed by the applicant and described and claimed herein is thus intended for finding the stability of two or more oils, such as different petroleum oils, or petroleum and shale oils, or distilled fractions of petroleum, or any mixture of any two or more hydrocarbons containing nitrogen, sulphur and oxygen contaminats, or mixtures of amphyphilic compounds, by the measurement of the chemical polarity of such mixtures of two or more components, by reversed-phase gas chromatography, is characterized in that it comprises:

a) finding the chemical polarity of each ingredient of the mixture, separately, by reversed-phase gas chromatography, whereby each oil alternately (petroleum oil, shale oil, distilled fraction of petroleum or of shale oil, or non-ionic surfactant) is used as the stationary phase, most polar of the oils (petroleum shale, distilled fraction of petroleum or shale oil, oil emulsion, or non-ionic surfactant) being picked as the reference;

b) plotting a graph of figures arrived at for chemical polarity of original oils along absicssas, and along ordinates the percentage by weight of the most polar of the oils, stability or quality of mixture being found from said graph along the straight line joining polarity of original oils to figure for acceptable chemical polarity for intended end use.

Alternatively the inventive process enables stability of original oils of a mixture to be found by means of a process which comprises:

a) preparing at least three mixtures of known concentration by weight of aforesaid oils or their fractions, each one of such mixtures to be consecutively employed as the stationary phase for the reversed-phase gas chromatography, in order to arrive at the chemical polarity of each oil mixture or fractions thereof;

b) plotting of a graph where the chemical polarity figures arrived at in a) for at least three mixtures are the abscissas and the percentage by weight of the most polar oil, between 0 and 100, are the ordinates;

c) finding out by linear extrapolation at abscissas, the chemical polarities for instances of 0% to 100% by weight of most polar oil, which will be the rates for the least and the most polar of the oils, respectively, that is, polarity of original oils or fractions thereof, unmixed.

Obviously the chemical polarity (or stability) of any intermediate mixture will be found graphically, figures lying among those for the chemical polarity of original oils, which will enable choice of the most suitably stable mixture for intended use to be made.

Thus this invention has an extremely wide range of use in the petroleum field, from the first working of deposits, to the finding of most suitable cuts in fractioning within cracking plants, and also as a paramenter in the making of mixtures of pre-established stability for given uses, or in the disposal of mixtures of various oils or fractions of hydrocarbons of unsuitable stability.

Furthermore the scope of the research work being done by the applicant in this field leads to expectations that finding of the chemical polarity of mixtures containing hydrocarbons and polar molecules may be extended to instances where the non-polar hydrocarbonic moiety and the polar heteroatomic moiety may be contained in the same molecule, as in the case of amphyphilic molecules, to which not only the non-ionic surfactants so much employed in the petroleum industry but also the many other organic compounds as well as pharmaceuticals and biologically active compounds belong, as long as non-ionic.

In view of the wealth of applications foreseeable for the process described and claimed herein, which applications go beyond the petroleum domain, it seems clear that the examples to be provided are just a small part of possible practical instances of this invention and should not therefore be regarded as limiting it.

BRIEF DESCRIPTION OF THE DRAWINGS

FIGS. 1, 2, 3, 4, and 5 show graphs of polar concentrations of various oils along ordinates and scale of chemical polarity along abscissas in accordance with the present invention.

PREFERRED EMBODIMENTS

In one of the preferred embodiments of this invention the finding of the chemical polarity of petroleum mixtures is aimed at, for the purpose, for example, of optimizing production and of making up mixtures to make refining easier. In the course of research done by the Applicant the question of how chemical polarities behaved in mixtures of several oils was looked into; whether or not such polarities represented additional properties, in an effort to arrive at parameters that might help in the estimating of polarity and therefore of the quality of the blends processed or exported.

EXAMPLES 1, 2 AND 3

Figure 1:
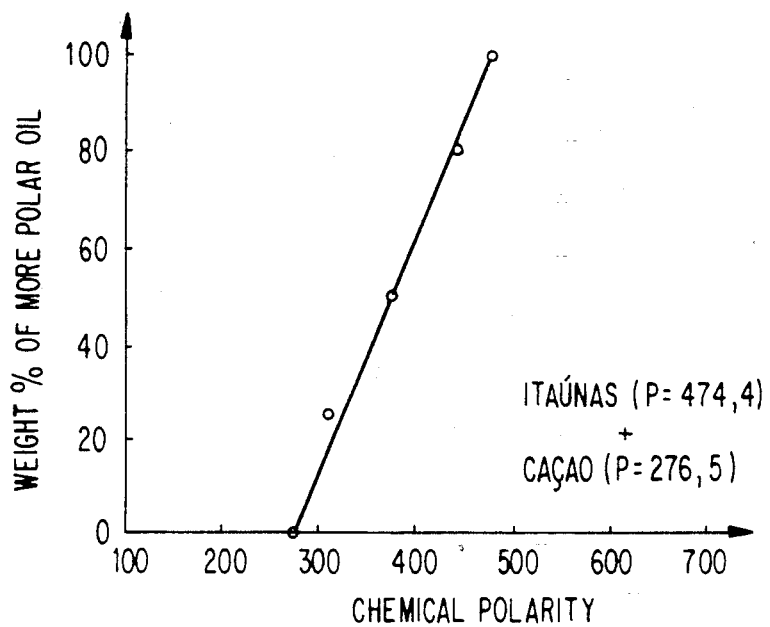

By means of the impregnation of a support containing, as its stationary phase, the 260° C. plus fraction of pure petroleum oils and their mixtures, respectively, in varying concentrations, the chemical polarity of petroleums from several sources and their mixtures was found according to the procedure described in Brazilian Application PI 8703790. FIG. 1 shows the chemical polarity of mixtures of petroleum oil that was found, the most polar having been the Itaûnas petroleum oil, at 474.5 and the least, a Cacao petroleum oil, at 276.5. As stated above, it can be graphically shown that a mixture containing 50% by weight of each of the oils has a chemical polarity of 375. If such polarity is enough chemical stability for a given application, a 1:1 mixture would be employed. However, if it does not stand for enough chemical stability for the required application, the chemical polarity limit standing for minimum required stability for the intended application would be picked from the graph and mixture would be made up in the exact proportions.

Figure 2:
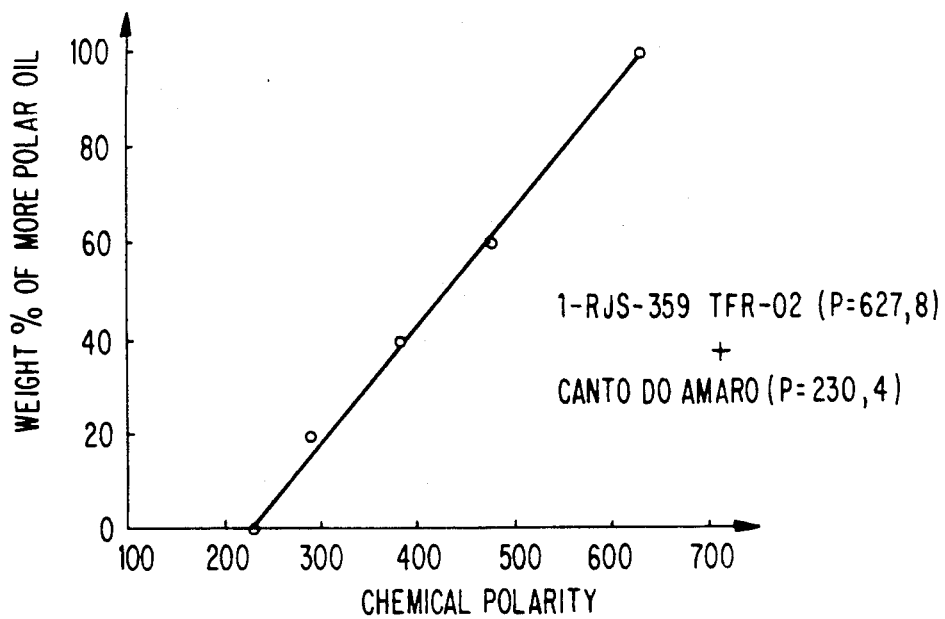

FIG. 2 is that of another graph for the process described herein, with pure original oils from 1-RJS-359 TFR-02 and Canto Do Amaro wells, the polarities of which are 627.8 and 230.4 respectively.

To arrive at FIGS. 1 and 2 a straight line is plotted on a graph starting from two points representing polarities of the original oils. Graph shows most polar concentrations of oil along ordinates and scale of polarity along abscissas. Concentrations and respective polarities are read off from such line.

Figure 3:
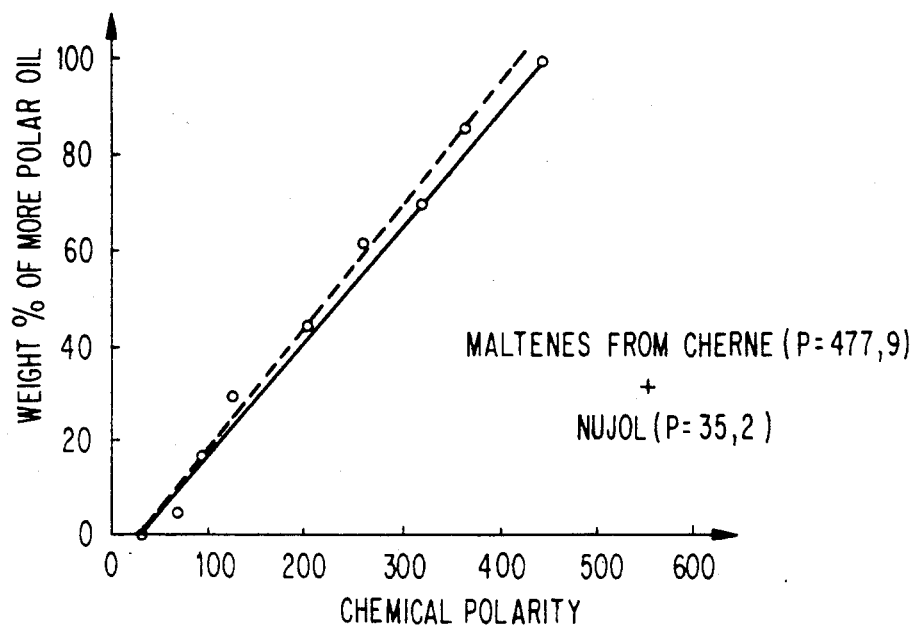

FIG. 3 shows application of such process for a fraction of Cherne petroleum oil, namely, the very high (455.9) polarity malthenes, diluted in nujol, and extremely low polarity (35.2) mineral oil. In this case, in order to check on the accuracy of the process, various proportions of the petroleum malthenes were added to the nujol and the polarities of the mixtures were reckoned, and broken line plotted; the bold line represents relation-relationship of Cherne petroleum malthenes and nujol in terms of original polarities. Formula for bold straight line is:

$$y = \frac{100}{P_1 - P_2} x - A$$

where y = concentration of most polar oil in mixture
x = polarity of mixture
$P_1$ = original polarity of most polar oil
$P_2$ = polarity of least polar original oil
A = value where bold line cuts axis of ordinates True figures found (broken line) and figures found from line plotted from original polarities (bold line) lie apart in places by about ±5%. It can therefore be said that the polarity of mixtures of petroleum oil or of fractions thereof can be estimated within ±5% of error, if polarities of original crudes (or of their fractions) of mixture are known. The opposite also applies.

From Examples 1, 2 and 3, shown in FIGS. 1, 2 and 3, one can conclude that:

- the polarities of petroleum oils or of their fractions, when mixed, are linearly related to the concentrations of petroleum oils or their fractions involved in such mixture;
- if original polarities of two petroleum oils or their fractions is known then the polarities of their mixtures in various concentrations can be found;
- if the polarities and concentrations of at least three mixtures are known then the polarities of the original oils or fractions thereof can be estimated.

Another form of this invention deals with finding the stability of mixtures of shale oil with petroleum oil, as well as comparing the stability and quality of shale oil derived from the various processes of working bituminous shale rock that have been developed in Brazil, namely, PETROSIX, PLASOL and FLOOD BED, with the stability and quality of various petroleum oils.

Example 4 below illustrates this embodiment of the present invention.

EXAMPLE 4

In this Example the chemical polarity of the shale oils derived from the shale rock working processes referred to above was measured. In the measurement of shale oil chemical polarities the basic procedure described under Brazilian Application PI 8704790 included measurement of interaction of the stationary phase as well (shale oil derived from the various kinds of processes), with compounds such as pyridine and triethylamine, since such compounds are to be found in considerable quantities admixed to shale oils. Comparison of the quality and stability of shale oils with quality and stability of petroleum oils likewise calls for the gauging of interaction between such amines and petroleum oils.

Hence the measured chemical polarity of the shale oils got by means of the various processes was as follows:

| | |
|---|---|
| Shale oil from FLOOD BED process | polarity 1182.6 |
| PETROSIX | polarity 1129.7 |
| PLASOL | polarity 1679.6 |

The polarity of the same oils, without taking interaction with such amines into account was 957.7, 900.7 and 1329.8 respectively. Thus, compared with petroleum oils from various sources, chemical polarities of which run from 211.3 (Rio Grande do Norte, Brazil) considered to be slightly polar, up to 896.6 (Boscan petroleum from Venezuela), looked upon as very polar, it is found that shale oils are even more polar, that is, more unstable and of higher polarity, therefore lower quality.

Figure 4:
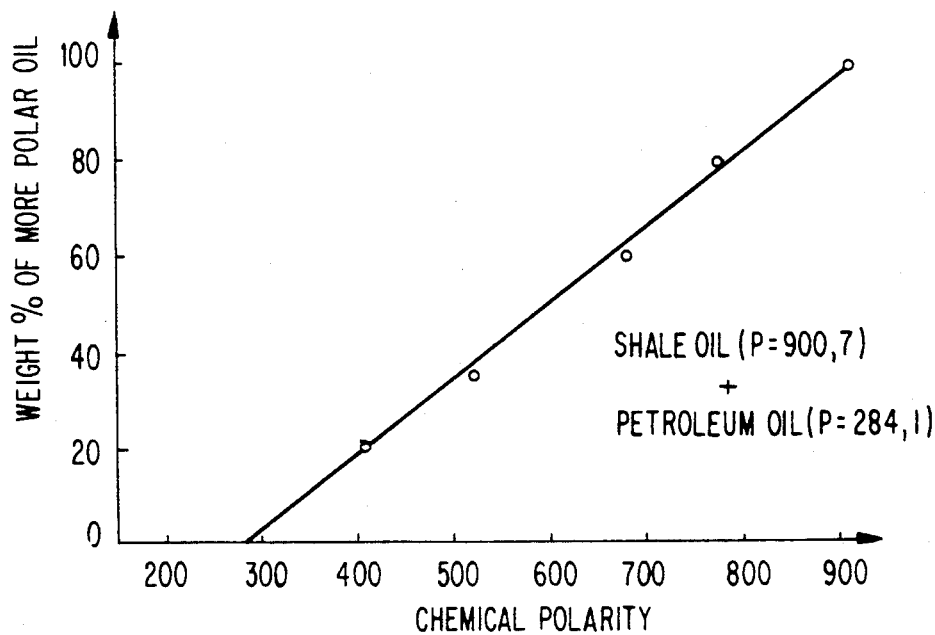

Therefore by measuring the chemical polarity of shale oils derived from the various processes, one can find, for example, the stability of mixtures of shale oil(s) with petroleum oils by finding the highest chemical polarity figure for a mixture of shale oil/petroleum that a given application can stand. FIG. 4 shows mixtures of 900.7 chemical polarity shale oil with 284.1 polarity petroleum oil. For instance, FIG. 4 shows that 20% of shale oil produced by the PETROSIX process can be added to a quite stable petroleum provided that for the intended application a mixture stability equal to a polarity of 400 can be withstood.

A further form of this invention is aimed at finding the stability of mixtures of fractions of medium and heavy distillates by finding the chemical polarity of such mixtures.

Hence this process to find the stability of oil mixtures can be applied to mixtures of fractions of medium and heavy distillates containing nitrogen, sulphur and oxygen contaminants.

Within the state of the art it is known that the nitrogen, sulphur and oxygen heteroatomic ingredients of petroleum render its fractions secured by distillation and catalytic processes impure. Such heteroatomic substances (alcohols, acids, thiophenes, benzothiophenes, amines, mercaptans, carbazoles, etc.) have several reactive organic functions that make petroleum products unstable, which instability is announced by a series of undesirable particulars, such as, colour, smell, caking, corrosion, etc., among commercial commodities. Therefore such heteroatomic ingredients have to be got rid of so as to enable petroleum products to be marketed within prevailing specifications.

Usually such compounds are got rid of by chemical, physico-chemical, or catalytic treatment action, involving, respectively, extraction with acids, bases and solvents, percolation through clay, hidrogenation, etc.

Quality of the products got is then evaluated by means of standard tests such as induction period, copper foil corrosion, degree of acidity, etc., or by elemental analysis whereby elimination of the element concerned is controlled, efficiency of such kinds of treatment being found through lowering of the quantity of such elements. However any presence of oxygenated compounds is not usually looked into since analysis is difficult; of these, acid content is the only one for which degree of acidity is gauged.

However the instability of mixtures of medium and heavy fractions of distillates can be worked out in a simple and precise way by means of the process described and claimed herein and used for mixtures of such distilled fractions by measuring the chemical polarity of the mixtures of distilled fractions contaminated by nitrogen, sulphur, and oxygen polar compounds.

The great usefulness of this process is seen in the monitoring of treatment operations, in comparison of the quality of catalytic cracking and hydrogentation charges and the quality of products therefrom, whether as a sole cut or as mixtures of cuts for end use.

Basically, in the reverse-phase gas chromatography process the medium distillate fractions for which stability and quality were to be found were used as the stationary phase, modifications having been introduced according to the degree of volatility of the fraction of mixture of fractions under study.

The following Examples show how the process herewith invented works when used for mixtures of several fractions of medium distillates.

EXAMPLE 5

In this Example the quality (stability) of diesel oil got by mixing several cuts (kerosene+light diesel oil+heavy diesel oil+heavy naphtha), referred to herein as line diesel, is compared with that of the light diesel oil of which it consisted originally.

To 50 ml of ordinary pentane 0.5 g of light diesel oil was added and this solution was poured upon 5.0 g of a 60/80 mesh Vollaspher $A_2$ support contained in a flask. Mixture was evaporated in a rotating evaporator at a reduced pressure of 17 mm of Hg. After solvent had been fully evaporated resultant matter was transferred into a porcelain dish and placed for about twelve hours, or throughout the night, in an oven, at a pressure of 10 mm of Hg. Matter got therefrom consisted of the filling of the chromatography column and was used to fill a stainless steel pipe 2 meters long and 3.2 mm in outside diameter, according to the usual procedure. The chromatography column so prepared was conditioned by a 20 ml/min flow of nitrogen and programmed temperature rise from 30° to 100° C. at a rate of 0.5° C./min., such final temperature of 100° C. having been kept up for four hours.

Column was thereupon cooled and flow adjusted to 10 ml/min. Temperatures at detector, injector and column during the test were kept at 250° C., 200° C., and 100° C., respectively.

A series of polar substances were then injected: -1-butanol, thiophene, dioxane, 2-methyl-2-pentanol, benzene, nitropropane, 2-pentanone and iodobutane, together with the methane (not retained chromatographically) in order to find the adjusted retention times for each polar substance. Ordinary paraffins (n-alkanes) were injected in the same way.

Retention times were calculated according to E. Kóvats in "Advances in Chromatography", J. C. Giddings and R. A. Keller, Editors, Marcel Dekker, Inc., New York, vol. I, 1965, p. 229, as follows:

$$I = \frac{100 \log x_i - \log x(n - C_z)}{\log x(n - C_{z+1}) - \log x(n - C_z)} + 100 \cdot z$$

where $x_i$ = tested solute adjusted retention time $x(n\text{-}C_z)$ = adjusted retention time of ordinary alkane eluted promptly before tested solute $x(N\text{-}C_{z+1})$ = adjusted retention time of ordinary alkane eluted immediately after tested solute A chromatographic column was then prepared, in the same way and to the same dimensions as for the former one, but stationary phase was a standard hydrocarbon-squalane-same solutes having been injected and retention times reckoned in the same fashion. With retention times from diesel oil sample and squalane the constants of W. O. McReynolds, as described in the Journal of Chromatographic Science, 1970, 8, p. 685, can be found:

$$\Delta I = I_o - I_{sq}$$

where $I_o$ and $I_{sq}$ are the Kóvats retention times for each solute in the light diesel oil and squalane columns respectively. Sum of I's for all solutes represents the relative polarity of light diesel oil in relation to the standard hydrocarbon-squalane-polarity of which is zero.

Polarity of light diesel measured this way was 146.3

Same procedure as above was followed to find chemical polarity of line diesel, which is a mixture of several distilled fractions. Figure found for line diesel was 297.5. Thus it was found that line diesel, which consists of several cuts together, was of considerably poorer quality and lower stability than light diesel oil. It was thus found that it is not advisable to blend several cuts together, such as kerosene with light diesel oil, heavy diesel oil and heavy naphtha (line diesel) where light diesel oil is regularly employed, since the fraction of the distillate got from the mixture has a stability which is unsuitable for the intended final use.

EXAMPLE 6

This Example serves to show how the procedure for two different blends of petroleum meant to produce aviation kerosene can lead to products of different stability, and how the process of this invention can help in choosing the best product in terms of intended use. Thus, starting with two blends of petroleum, kerosene A of 84.0 chemical polarity and kerosene B of 128.7 chemical polarity were produced. Because of the strictness recommended in choosing this kind of fuel the best quality fuel, kerosene A, was chosen without any hesitation, which was more stable because of its lower chemical polarity. Of course a top chemical polarity figure could also have been quoted, for a mixture of the two kerosenes, for instance, 100, which could have been arrived at by mixing the two types of kerosene—A and B—in suitable proportions, to be found from the corresponding graph.

EXAMPLE 7

This Example shows how, from among several different blends of petroleum, the most suitable charge, since most stable, can be chosen for an operation such as, for instance, catalytic cracking, usually along with sensitive expensive catalysts. For example, in a given refinery there were three blends of petroleum available, and it had to be found which of these was best for fluid catalytic cracking purposes along with a very sensitive and expensive catalyst. The chemical polarity of each of the A, B and C gasoils was found, which were 364.9, 397.2 and 420.3, respectively, which showed that gasoil A was the most stable and suitable for the operation to be undertaken. Upon finding the other particulars of the charges, the fitness of the polarity figures in terms of heteroatomic content is to be seen.

|  | GASOILS | | |
|---|---|---|---|
|  | A | B | C |
| Density (gm/cm$^3$) | 0.9243 | 0.9318 | 0.9437 |
| Sulphur (% by weight) | 0.94 | 0.98 | 0.92 |
| Nitrogen (% be weight) | 0.18 | 0.20 | 0.24 |
| Polynuclear aromatic hydrocarbons (mmol/100 g) | 38.0 | 39.0 | 39.5 |
| Polarity | 364.9 | 397.2 | 420.3 |

EXAMPLE 8

This Example shows that medium petroleum distillates of polarities very close to one another may exhibit chemical polarities that are quite a lot different, which may be important when choosing a given cut of petroleum or when choosing a mixture of cuts, polarity and stability of which have been fixed beforehand. For instance, the chemical polarity of two petroleums, A and B, was found to be 418.4 and 427.8, respectively, thus very much alike. Surprisingly, cuts of petroleum A and B in the 176.6° to 371.0° C. (350°-700° F.) range showed chemical polarities of 316.1 and 268.0, respectively, pointing to petroleum B as being the most suitable for intended use.

The embodiment shown next is generally like the process invented, since it has been shown that the stability of mixtures of different types of oils as well as mixtures of their fractions can be found unerringly by such process. The following Example shows that the notion of "stability of oil mixtures" can be applied not only to mixtures of several kinds of oils but also to mixtures of distillates, which includes 'mixtures' where the hydrocarbon moiety and the heteroatomic moiety are in the same molecule, it being likewise possible to find the stability of any such substance or mixture of substances, provided they are non-ionic, by means of the process herein described and claimed.

EXAMPLE 9

This Example therefore bears witness to the broad scope of the notion of 'mixture', inasmuch as the process applies not only to mixtures of different oils and their fractions but also to certain types of substances (and their mixtures as well), containing a non-polar hydrocarbon moiety and a polar heteroatomic moiety in the same molecule.

Though this process is not to be regarded as limited to the substances referred to below the applicant has concerned itself with the aforesaid notion of chemical polarity as regards non-ionic surfactants, which are used to a great extent in the petroleum industry, since such non-ionic surfactants are amphyphilic substances, that is, substances where one moiety of their molecules is a non-polar hydrocarbon and the other a polar heteroatom.

Every year the treatment of petroleums uses up a huge quantity of surfactants, intended to separate emulsions of water and oil. The state of the art concerned in this field of study recommends that the polarity of the demulsifier should be higher than that of the natural petroleum surfactants, so as to be able to disperse them from the water-oil interface. The higher the polarity of a petroleum the likelier it is to emulsify water so that a suitable demulsifier must have a polarity that is higher still if it is to break up the emulsion. Knowledge of the polarity of the demulsifiers was always a major need in the technique employed but experimental difficulties made it hard to find. Even the classifying of surfactants in terms of the hydrophylic-lipophylic scale (HLB) lacks precision and is limited.

Now, most of the surfactants employed in the petroleum industry are amphyphilic compounds, that is, they exhibit dual affinity—for polar and non-polar solvents—since their molecules consist of a polar moiety, made up of heteroatoms (usually O, S, N, P, Cl) belonging to several functional organic groups (alcohol, ether, acid, ester, thiol, sulphonate, sulphate, amine, phosphate, etc.) and a non-polar moiety, usually a long ordinary paraffin chain, occasionally with cycloparaffinic or aromatic groups in it. Because of these features the amphyphilic molecules, within either medium, polar or non-polar (water and oil systems), migrate to the interface of such mediums, where they likewise satisfy molecular interaction affinities. A greater or a lesser affinity for one or the other of the mediums will depend on the extension and type of the polar and non-polar moities of the molecules.

It is important to find the chemical polarity of surfactants not only in the case of one only surfactant but also in that of mixtures thereof, since where mixtures of compounds are concerned use may be made of the synergistic effect of their molecules.

In finding the chemical polarity of pure non-ionic surfactants or those within synergistic mixtures with the aid of inverse gas chromatography, the support referred to in previous Examples herein is covered with the surfactant the chemical polarity of which is being sought, such surfactant having first of all been dissolved in a suitable solvent. The stationary phase is thereby got and it is put in interaction with several solutes, as already described. The same interactions were measured for squalane, polarity of which is zero.

In order to show that the chemical polarity results for non-ionic surfactants got with this process are in line with HLB scale figures usually adopted for surfactants, FIG. 5 was drawn up which serves to bear out the linear relationship between experimental values and HLB data supplied by manufacturers for the products concerned.

Results serve to show that this process is useful as a substitute for the HLB scale, and is a more precise means of discovering the behaviour of non-ionic surfactants as regards polarity. Hence by measuring the chemical polarity of a surfactant or its mixtures the most suitable surfactant or mixture of surfactants may be accurately picked for the required purpose.

Measurement repeatability is excellent, being ±0.56%, thus bearing witness to the reliability of such experimental procedure.

in Table 1 below chemical polarity figures are given for commercial non-ionic surfactants, together with HLB figures provided by manufacturer.

TABLE 1

| SURFACTANT | HLB(*) | RELATIVE POLARITY (**) |
|---|---|---|
| RENEX 40 | 9.0 | 1 784.2 |
| RENEX 60 | 10.9 | 2 012.4 |
| RENEX 120 | 14.1 | 2 294.7 |
| RENEX 150 | 15.0 | 2 496.7 |
| RENEX 300 | 17.1 | 2 879.1 |
| SPAN 20 | 8.6 | 1 575.2 |
| SPAN 40 | 6.7 | 1 310.8 |
| TWEEN 20 | 16.7 | 2 883.8 |
| TWEEN 40 | 15.6 | 2 511.6 |
| TWEEN 60 | 14.9 | 2 301.8 |

(*)Figures provided by manufacturers
(**)Average figure after three readings

Therefore the process covered herein is useful in comparing the polarity of petroleum oils and those of surfactants and their mixtures. Brazilian petroleum polarities range from 43.5 for the more non-polar petroleum from Bahia to 627.0 for a polar petroleum from the Campos basin in Rio de Janeiro. On the other hand the polarity figures found for surfactants, as shown in the table above, lie all of them above 1000, measurement having been made, for the first time, of that which demulsification theory claimed, and it having been found that the polarity of surfactants is really much higher than that for petroleum oils.

The feasibility of the present system for finding the stability of mixtures of oils and of fractions thereof is of major importance in the present critical state of the oil business since it enables stability to be found for mixtures of oils from the most different of sources, as in the case of oils derived from the distillation of coal (Synthoil), where maximum proportion of which to be added to petroleum, without harming the stability of the mixture, can be accurately found by the present process for each kind of application, thereby upgrading organic substances which have until recently been little used on an industrial scale.

The variety of Examples provided without exhausting the subject however, enables the extremely wide scope of the process described and claimed herein to be perperceived, a process which can be employed for all kinds of mixtures of oils from various sources, or fractions thereof, and of mixtures in general of substances containing non-polar and polar moieties, which moieties may lie within different molecules or even within one same molecule. Hence, application of the present process may be extended to fields other than the petroleum field, such as surfactants, pharmaceuticals, biotechnological, etc., whenever the chemical polarity of a non-ionic mixture of polar/non-polar substances has to be found.

I claim:

1. Process to find the stability of mixtures of oils; whereby such process comprises:
    a) separately finding the chemical polarity of each component of the mixture of oils or of the fractions thereof, by reversed-phase gas chromatography, each oil being employed alternately as a stationary phase, selecting the most polar of the oils to be used as the reference oil;
    b) plotting chemical polarity figures on a graph found for the original oils or fractions thereof under step a), such polarity figures being represented by the graph abscissa and the percentage of most polar oil by weight, ranging from 0 to 100, being represented by the graph ordinate, and determining the stability of quality of the mixture of oils, or of fractions thereof, on the aforesaid graph upon a straight line joining polarities of the original oils and the acceptable chemical polarity figure for final intended use.

2. Process to find the stability of mixtures of oils, according to claim 1, whereby the mixture of oils covers two or more petroleum oils from different sources.

3. Process to find the stability of mixtures of oils, according to claim 1, whereby the mixture of oils covers two or more shale oils or mixtures of petroleum oils and shale oils.

4. Process to find the stability of mixtures of oils, according to claim 1, whereby the mixture of oils covers a mixture of two or more distilled fractions of petroleum or shale oils.

5. Process to find the stability of mixtures of oils, as in claim 1, whereby the mixture covers two or more non-ionic compounds containing a non-polar hydrocarbon moiety and a nitrogen, sulphur or oxygen polar moiety in the same or different molecules.

6. Process to find the stability of mixtures of oils, as in claim 1, whereby stability of mixture of at least two oils is an inverse function of the concentration by weight of the most polar oil in the mixture.

7. Process to find the stability of mixtures of oils, whereby such process comprises:
    a) preparing at least three mixtures of known concentration by weight of the aforesaid oils, or fractions thereof, each one of the mixtures to be consecutively employed as a stationary phase for reversed-phase gas chromatography, in order to find the chemical polarity of each mixture of oils, or fractions thereof;
    b) plotting on the graph, where figures for chemical polarity arrived at in step a) for at least three mixtures, are the abscissa and percentage by weight for the most polar oil, from 0 to 100, are the ordinate;
    c) determining stability by linear extrapolation of chemical polarity along the abscissa, the abscissa ranging from the chemical polarity of the least polar oil to the most polar oil, respectively.

8. Process to find the stability of mixtures of oils, according to claim 7, whereby the mixture of oils covers two or more petroleum oils from different sources.

9. Process to find the stability of mixtures of oils, according to claim 7, whereby the mixture of oils covers two or more shale oils or mixtures of petroleum oils and shale oils.

10. Process to find the stability of mixtures of oils, according to claim 7, whereby the mixture of oils covers a mixture of two or more distilled fractions of petroleum or shale oils.

11. Process to find the stability of mixtures of oils, according to claim 7, whereby the mixture of oils covers two or more non-ionic compounds containing a non-polar hydrocarbon moiety and a nitrogen, sulfur or oxygen polar moiety in the same or different molecules.

12. Process to find the stability of mixtures of oils, according to claim 7, whereby stability of mixture of at least two oils is an inverse function of the concentration by weight of the most polar oil in the mixture.

* * * * *

UNITED STATES PATENT AND TRADEMARK OFFICE
CERTIFICATE OF CORRECTION

PATENT NO. : 5,163,982

DATED : November 17, 1992

INVENTOR(S) : Inai M. R. de Andrade Brüning

It is certified that error appears in the above-identified patent and that said Letters Patent is hereby corrected as shown below:

On the title page: Item [19] delete "Bruüning" and insert --Brüning--;

Column 1, section [75], delete "Bruüning" and insert --Brüning--.

Signed and Sealed this

Seventh Day of December, 1993

Attest:

BRUCE LEHMAN

Attesting Officer

Commissioner of Patents and Trademarks